(12) United States Patent
Giraudi et al.

(10) Patent No.: US 7,105,686 B2
(45) Date of Patent: Sep. 12, 2006

(54) MANUFACTURE OF TOCOL, TOCOL DERIVATIVES AND TOCOPHEROLS

(75) Inventors: Lisa Giraudi, Huningue (FR); Werner Bonrath, Freiburg (DE)

(73) Assignee: DSM IP Assets B.V., Heerlen (NL)

( * ) Notice: Subject to any disclaimer, the term of this patent is extended or adjusted under 35 U.S.C. 154(b) by 169 days.

(21) Appl. No.: 10/916,274

(22) Filed: Aug. 11, 2004

(65) Prior Publication Data

US 2005/0038269 A1 Feb. 17, 2005

(30) Foreign Application Priority Data

Aug. 13, 2003 (EP) .................... 03018367

(51) Int. Cl.
*C07D 311/72* (2006.01)

(52) U.S. Cl. ...................... 549/408; 549/408
(58) Field of Classification Search ................. 549/408
See application file for complete search history.

(56) References Cited

FOREIGN PATENT DOCUMENTS

| EP | 658 552 A1 | 6/1995 |
|----|------------|--------|
| EP | 694 541 A1 | 1/1996 |
| EP | 694 541 B1 | 3/2000 |
| EP | 1 180 517 A1 | 2/2002 |

OTHER PUBLICATIONS

Hamidi and Pascal, "Synthesis and Structural Characterization of Some Anhydrous Ln(OTf)$_3$ Complexes (Ln=Sc, La, Nd, Sm, Gd, and Er; OTf=CF$_3$SO$_3$)," *Polyhedron*, vol. 13, No. 11, pp. 1787-1792 (1994).
Schager and Bonrath, "Synthesis of D,L-α-tocopherol Using 'Microencapsulated' Catalysts," *Applied Catalysis A: General*, vol. 202, pp. 117-120 (2000).
Schager and Bonrath, "Synthesis of D,L-α-tocopherol using Strong Solid Acids as Catalysts," *Journal of Catalysis*, vol. 182, pp. 282-284 (1999).
Ullmann's Encyclopedia of Industrial Chemistry, vol. A27, 5$^{th}$ edition, pp. 484-485, VCH Verlagsgesellschaft mbH, Weinheim (1996).

*Primary Examiner*—Taofiq Solola
(74) *Attorney, Agent, or Firm*—Bryan Cave LLP

(57) ABSTRACT

The present invention is concerned with a novel process for the manufacture of tocol, tocol derivatives and tocopherols, especially α-tocopherol, by the reaction of a hydroquinone featuring 0 to 3 methyl groups, especially 2,3,5-trimethylhydroquinone, with isophytol, phytol or a(n) (iso)phytol derivative, most preferably with isophytol, in the presence of gadolinium trifluoromethanesulfonate, Gd(OSO$_2$CF$_3$)$_3$, as the catalyst in a biphasic solvent system. This biphasic solvent system consists essentially of a polar organic solvent and a non-polar organic solvent. The polar organic solvent is preferably ethylene carbonate and/or propylene carbonate. The non-polar solvent is preferably at least a solvent selected from the group consisting of hexane, heptane, octane, cyclohexane and methylcyclohexane.

26 Claims, No Drawings

MANUFACTURE OF TOCOL, TOCOL DERIVATIVES AND TOCOPHEROLS

The present invention is concerned with a novel process for the manufacture of tocol, tocol derivatives and tocopherols as those e.g. disclosed on page 5, third paragraph of DE-OS 21 60 103, especially α-tocopherol (TCP), by the reaction of a hydroquinone featuring 0 to 3 methyl groups, especially 2,3,5-trimethylhydroquinone (TMHQ), with phytol (PH) or a phytol derivative, e.g. isophytol (IP) or a(n) (iso)phytyl compound, in the presence of gadolinium trifluoromethanesulphonate, $Gd(OSO_2CF_3)_3$, as the catalyst in a biphasic solvent system.

As is known, (all-rac)-α-tocopherol (or as it has mostly been denoted in the prior art, "d,l-α-tocopherol") is a mixture of four diastereomeric pairs of enantiomers of 2,5,7,8-tetramethyl-2-(4',8',12'-trimethyl-tridecyl)-6-chromanol (α-tocopherol), which is the biologically most active and industrially most important member of the vitamin E group.

Many processes for the manufacture of "d,l-α-tocopherol" (referred to as such in the literature reviewed hereinafter) by the reaction of TMHQ with IP or PH in the presence of a catalyst or catalyst system and in a solvent or solvent system are described in the following selected literature.

EP-A 0 658 552 discloses a process for the preparation of α-tocopherol and derivatives thereof, wherein fluorosulfonates $[M(RSO_3)_3]$, nitrates $[M(NO_3)_3]$ and sulfates $[M_2(SO_4)_3]$ are used as the catalysts with M representing a Sc, Y or lanthanide atom, and R representing fluorine, a fluorinated lower alkyl group or an aryl group which may be substituted by one or more fluorine atoms. The reaction is carried out in a solvent which is inert to the catalyst and the starting materials, TMHQ and allyl alcohol derivatives or alkenyl alcohols, examples of the solvent being aromatic hydrocarbons, linear and cyclic ethers, esters and chlorinated hydrocarbons. Preferably the allyl alcohol derivatives or alkenyl alcohols are used in a molar excess of 4% or 10% compared to TMHQ.

According to EP-B 0 694 541 a carbonate ester, a lower fatty acid ester or a mixed solvent of a non-polar solvent and a lower $C_{1-5}$-alcohol is used as solvent for the preparation of TCP. As the catalyst a mineral acid, a Lewis acid, an acidic ion exchange resin or a triflate, nitrate or sulfate of Sc, Y or a lanthanid element is used. The starting materials, TMHQ and IP, PH or a PH derivative, are preferably used in equimolar amounts.

In the process of EP-A 1 180 517 TMHQ and IP or PH are reacted in the presence of a bis(perfluorinated hydrocarbyl sulphonyl)imide or a metal salt thereof to obtain TCP. Solvents for this reaction are polar organic solvents such as aliphatic and cyclic ketones, aliphatic and cyclic esters and carbonates, and non-polar organic solvents such as aliphatic and aromatic hydrocarbons or mixtures thereof.

In Applied Catalysis A: General 202 (2000), pages 117 to 120 "microencapsulated" (MC) catalysts, MC-$(F_3CSO_2)_2$NH and MC-$Sc(OSO_2CF_3)_3$, are used for the synthesis of TCP starting from TMHQ and IP. Unfavourably the MC-catalysts cannot be recycled and loose their activity after a single employment.

Journal of Catalysis 182, 282–284 (1999) describes the use of heterogeneous solid acid catalysts such as Nafion® NR 50, a copolymer of tetrafluoroethene and a perfluorosulfonylether, or Amberlyst® 15, a strongly acidic cation exchange resin with $SO_3H$ functional groups, for the TCP synthesis. These catalysts however are rather expensive.

To obtain tocol, tocol derivatives and tocopherols such as α-tocopherol according to the processes of DE-OS 21 60 103 as well as U.S. Pat. No. 3,789,086 compounds of the following formula

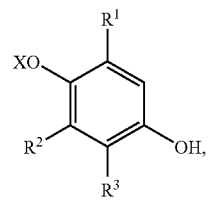

wherein X is hydrogen, alkanoyl or aroyl, and $R^1$, $R^2$ and $R^3$ are individually hydrogen or methyl, are reacted with compounds of the following formulae

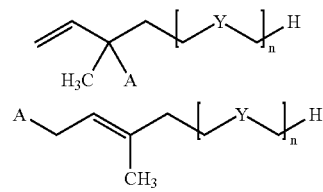

wherein Y is —$CH_2$—$CH(CH_3)$— or —CH=$C(CH_3)$— and A is halogen, hydroxy, etherified hydroxy or esterified hydroxy in the presence of HCl and Fe and/or $FeCl_2$ as the catalyst.

The object of the present invention is to provide a process for the manufacture of tocol, tocol derivatives and tocopherols, especially α-tocopherol, by using a catalyst and a solvent wherein the catalyst used has no, or at least a much reduced, corrosive action, is non-toxic and not expensive, does not contaminate the environment, and catalyzes the desired reaction as selectively as possible and in high yields. Furthermore, the catalyst should be readily separable and re-usable several times.

The object of the present invention is achieved by the reaction of a compound a) of the formula (II) with $X^1$, $X^2$ and $X^3$ being independently from each other hydrogen or methyl,

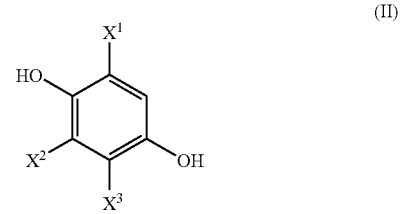

i.e. a hydroquinone featuring 0 to 3 methyl groups namely TMHQ (formula (II) with $X^1$=$X^2$=$X^3$=methyl), 2,3-dimethylhydroquinone, 2,5-dimethylhydroquinone, 2,6-dimethylhydroquinone, 2-methylhydroquinone or hydroquinone, preferably by the reaction of TMHQ, with a compound b) selected from the group consisting of PH (formula (IV) with R=OH), IP (formula (III) with R=OH), and (iso)phytyl derivatives represented by the following formulae (III) and (IV) with R=C$_{2-5}$-alkanoyloxy, benzoyloxy, methanesulfonyloxy (=mesyloxy), benzenesulfonyloxy or toluenesulfonyloxy (=tosyloxy),

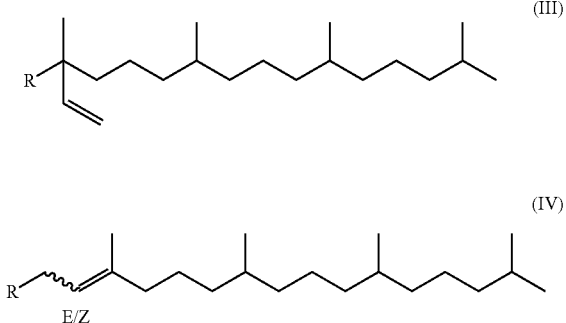

compound b) preferably selected from the group consisting of PH, IP and (iso)phytol derivatives represented by the formulae (III) and (IV) with R=acetyloxy or benzoyloxy, more preferably selected from the group consisting of PH and IP, most preferably with IP, by using gadolinium trifluoromethanesulphonate, Gd(OSO$_2$CF$_3$)$_3$, as the catalyst in a biphasic solvent system to obtain a compound of the following formula (I) (a tocol, a tocol derivative or a tocopherol) with X$^1$, X$^2$ and X$^3$ being independently from each other hydrogen or methyl, preferably with X$^1$, X$^2$ and X$^3$ being all methyl (=TCP),

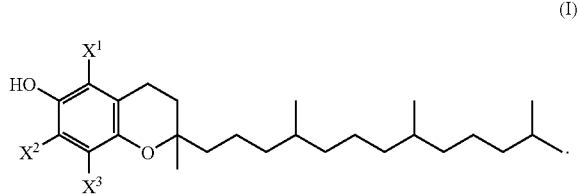

Concerning the substituent R: Preferred examples for "C$_{2-5}$-alkanoyloxy" are acetyloxy, propionyloxy and pivaloyloxy.

While the production of (a) (all-rac)-tocol (derivative) or (all-rac)-tocopherol, especially (all-rac)-α-tocopherol, is preferred, the invention is not limited to the production of that particular isomeric form and other isomeric forms can be obtained by using phytol, isophytol or a derivative thereof as the starting material in the appropriate isomeric form. Thus, (RS,R,R)-α-tocopherol e.g. will be obtained when using (R,R)-phytol, (R,R,R)-isophytol, (S,R,R)-isophytol or (RS,R,R)-isophytol or an appropriate (iso)phytol derivative and TMHQ. The same applies for the manufacture of the other chiral tocol (derivative)s and tocopherols.

In an especially preferred embodiment of the invention TMHQ is reacted with PH and/or IP, more preferably with IP, to TCP.

The catalyst Gd(OSO$_2$CF$_3$)$_3$, which can be obtained e. g. according to a procedure described by Moulay El Mustapha Hamidi and Jean-Louis Pascal in Polyhedron 1994, 13(11), 1787–1792 and which is also commercially available, can be used in solid form, as well as in solution or as suspension.

Preferably the catalyst is dissolved or suspended in the organic polar solvent, which is a part of the biphasic solvent system (see below), in which the reaction is carried out. The concentration of the solution is not critical. Furthermore, the catalyst tolerates traces of protic solvents such as methanol, ethanol and water. After the termination of the reaction the catalyst can be recycled with the polar phase.

The biphasic solvent systems suitable for the reaction of compound a), preferably TMHQ, and compound b) to tocol, a tocol derivative or a tocopherol such as TCP according to the present invention are mixtures of polar non-protic organic solvents such as cyclic carbonates, especially ethylene carbonate, propylene carbonate and 1,2-butylene carbonate, and non-polar solvents such as linear, branched or cyclic C$_{5-15}$-alkanes, especially linear, branched or cyclic C$_{6-10}$-alkanes.

Especially preferred polar non-protic organic solvents are ethylene carbonate and propylene carbonate.

Particularly preferred non-polar solvents are hexane, heptane, octane, cyclohexane and methylcyclohexane or mixtures thereof The most preferred non-polar solvent is heptane.

The most preferred biphasic solvent systems are mixtures of ethylene carbonate and/or propylene carbonate and hexane, heptane or octane, especially mixtures of ethylene carbonate and heptane, mixtures of propylene carbonate and octane, and mixtures of ethylene carbonate, propylene carbonate and heptane.

Conveniently the molar amount of compound a) (especially TMHQ) is at least about 25% higher than the molar amount of compound b). Preferably the molar ratio of compound a) to compound b) in the reaction mixture varies from about 1.25:1 to about 3:1, more preferably from about 1.35:1 to about 2.2:1, most preferably from about 1.5:1 to about 2:1.

The amount of the catalyst Gd(OSO$_2$CF$_3$)$_3$ used is based on the amount of compound b) which is used in the lesser molar amount. Usually the relative amount of Gd(OSO$_2$CF$_3$)$_3$ to the amount of compound b) is from about 0.1 to about 1.8 mol %, preferably from about 0.5 to about 1.5 mol %, more preferably from about 0.8 to about 1.2 mol %. Such amounts of Gd(OSO$_2$CF$_3$)$_3$ are sufficient to obtain high yields of desired product. In this context the expression "amount of Gd(OSO$_2$CF$_3$)$_3$" is to be understood as referring to the weight of pure gadolinium trifluoromethanesulphonate present, even though the catalyst may be impure and/or in the form of an adduct with a solvent. The synthesis of adducts is e.g. described in U.S. Pat. No. 3,615,169.

In the biphasic solvent systems the amount of polar solvent to the amount of non-polar solvent varies conveniently from about 5:1 to about 1:10 by volume, preferably from about 3:1 to about 1:5 by volume, more preferably from about 2:1 to about 1:1.25 by volume. The amount of the polar solvent used is conveniently from about 0.5 ml to about 2.0 ml, preferably from about 0.6 ml to about 1.75 ml, more preferably from about 0.8 ml to about 1.6 ml, based on 1 mmol of compound b).

It is an advantage of the present invention that the cyclic carbonate used in the biphasic solvent system and the non-reacted compound a) such as TMHQ can be recycled. Therefore, a preferred embodiment of the present invention is a process for the manufacture of a compound of the formula (I) (a tocol, a tocol derivative or a tocopherol), preferably TCP,

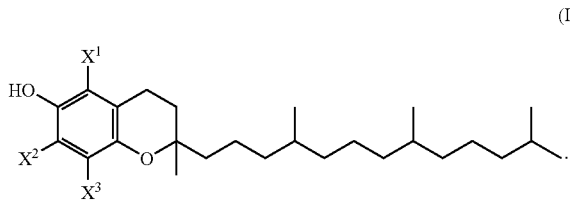

comprising the following steps:
i) reacting of a compound a) of the formula (II) with $X^1$, $X^2$ and $X^3$ being independently from each other hydrogen or methyl, preferably of TMHQ,

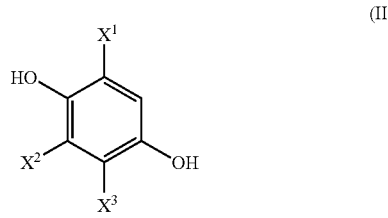

with a compound b) selected from the group consisting of PH, IP and (iso)phytol derivatives represented by the following formulae (III) and (IV) with $R=C_{2-5}$-alkanoyloxy, benzoyloxy, mesyloxy, benzenesulfonyloxy or tosyloxy

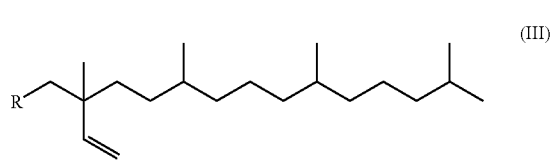

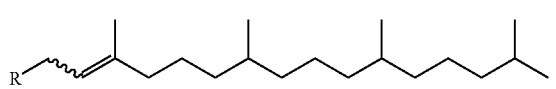

in the presence of gadolinium trifluoromethanesulphonate, $Gd(OSO_2CF_3)_3$, as the catalyst in a biphasic solvent system consisting essentially of a polar organic solvent and a non-polar organic solvent,
wherein the compound a), preferably TMHQ, is dissolved or suspended in the polar organic solvent, and the molar amount of the compound a), especially the molar amount of TMHQ, is at least about 25% higher than the molar amount of compound b), preferably the molar ratio of the compound a) to compound b) present in the reaction mixture is from about 1.25:1 to about 3:1, more preferably from about 1.35:1 to about 2.2:1, most preferably from about 1.5:1 to about 2:1;
ii) separating the polar phase containing the polar organic solvent, the catalyst, and non-reacted compound a) such as TMHQ from the non-polar phase containing the non-polar organic solvent and the produced compound of the formula (I) (tocol (derivative) or tocopherol);
iii) recycling the polar phase back in step i) of the process.

The reaction of a compound a), preferably TMHQ, with compound b) is conveniently carried out at temperatures from about 80° C. to about 160° C., preferably from about 90° C. to about 150° C., more preferably from about 100° C. to about 145° C.

The pressure under which the reaction of the compound a), preferably TMHQ, with compound b) is carried out is not critical, but the reaction is conveniently carried out at atmospheric pressure.

Moreover, the process according to the invention is conveniently carried out under an inert gas atmosphere, preferably gaseous nitrogen or argon.

The actual reaction of the compound a), preferably TMHQ, with compound b) generally lasts for about 2 to about 24 hours, preferably for about 3 to about 23 hours, especially for about 4 to about 22 hours.

The processes in accordance with the invention can be carried out batchwise or continuously, and in general operationally in a very simple manner, for example (1) by adding compound b) portionwise or continuously to a mixture of the non-polar solvent (such as mentioned above) and a solution/suspension of $Gd(OSO_2CF_3)_3$ and compound a), in the polar solvent (such as mentioned above).

A further possibility is (2) the portionwise or continuous addition of a solution of compound b) in the non-polar solvent (such as mentioned above) to a mixture of $Gd(OSO_2CF_3)_3$ and compound a), each dissolved or suspended in the polar solvent such as mentioned above.

It is also possible (3) to add, portionwise or continuously, a mixture of $Gd(OSO_2CF_3)_3$ and compound a)—each dissolved or suspended in the polar solvent—to compound b), dissolved in the non-polar solvent, or (4/5) to a mixture of the compound a), dissolved or suspended in the polar solvent, and compound b), dissolved in the non-polar solvent. The operational variants (4) and (5) can be carried out as follows:

(4) To a mixture of compound b), dissolved in the non-polar solvent, and a substantially equimolar amount of compound a), dissolved or suspended in the polar solvent, a mixture of $Gd(OSO_2CF_3)_3$ and compound a), each dissolved or suspended in the polar solvent, is added. The added amount of compound a) is here the substantial excess amount of compound a) over the employed amount of compound b).

(5) To a mixture of compound b), dissolved in the non-polar solvent, and compound a), dissolved or suspended in the polar solvent, whereby the amount of compound a) is the substantial excess amount of compound a) over the employed amount of compound b), is added a mixture of $Gd(OSO_2CF_3)_3$ and compound a), each dissolved or suspended in the polar solvent. The added amount of compound a) is here substantially the equimolar amount relative to the employed amount of compound b).

It is also possible to add, portionwise or continuously, compound a)—dissolved or suspended in the polar solvent—or a mixture of $Gd(OSO_2CF_3)_3$ and compound a)—each dissolved or suspended in the polar solvent—to a mixture of compound b), dissolved in the non-polar solvent, and $Gd(OSO_2CF_3)_3$ and compound a)—each dissolved or suspended in the polar solvent. This can be carried out in three different ways:

(6) To a mixture of compound b), dissolved in the non-polar solvent, and $Gd(OSO_2CF_3)_3$ and compound a), each dissolved or suspended in the polar solvent, whereby the amount of compound a) is the substantial excess amount of compound a) over the employed amount of compound b), is added a solution or suspension of compound a) in the polar solvent. The added amount of compound a) is here substantially the equimolar amount relative to the employed amount of compound b).

(7) To a mixture of compound b), dissolved in the non-polar solvent, and $Gd(OSO_2CF_3)_3$ and a substantially equimolar amount of compound a), each dissolved or suspended in the polar solvent, is added a solution or suspension of compound a) in the polar solvent. The added amount of compound a) is here the substantial excess amount of compound a) over the employed amount of compound b).

(8) To a mixture of compound b), dissolved in the non-polar solvent, and $Gd(OSO_2CF_3)_3$ and compound a), each dissolved or suspended in the polar solvent, whereby the amounts of $Gd(OSO_2CF_3)_3$ and compound a) in this mixture are less than their total amounts used in the reaction, are added further amounts of $Gd(OSO_2CF_3)_3$ and compound a), each dissolved or suspended in the polar solvent. Preferably the polar solution containing $Gd(OSO_2CF_3)_3$ and compound a), with which the reaction is started, and the added polar solution containing $Gd(OSO_2CF_3)_3$ and compound a) have the same concentration.

Furthermore (9) a solution/suspension of $Gd(OSO_2CF_3)_3$ in the polar solvent can be added to the biphasic mixture of a solution/suspension of compound a) in the polar organic solvent and a solution of compound b) in the non-polar organic solvent.

Preferred are methods (1) and (9), most preferred is method (1).

The rate of addition of the one component to the other is not critical. Conveniently, the component to be added is added continuously over a period from about 20 to about 90 minutes, preferably from about 25 to about 75 minutes, more preferably from about 30 to about 60 minutes, independently of the scale in which the process is performed.

The concentration of compound b), dissolved in the non-polar solvent, is conveniently from about 5 to about 35% by weight, preferably from about 10 to about 30% by weight, more preferably from about 15 to about 25% by weight, based on the total weight of the solution.

The concentration of compound a), dissolved or suspended in the polar solvent (with or without $Gd(OSO_2CF_3)_3$), usually ranges from about 5 to about 25% by weight, preferably from about 5 to about 20% by weight, more preferably from about 10 to about 17% by weight, (in each case) based on the total weight of the solution.

After completion of the addition of the solution/suspension of compound b) or the solution/suspension of compound a) or the solution/suspension of the mixture of $Gd(OSO_2CF_3)_3$ and compound a) and an appropriate subsequent reaction period, the two phases of the biphasic solvent system are separated from each other: The polar phase containing the polar organic solvent, the non-reacted compound a) and the catalyst is advantageously recycled. The isolation of the product (the compound of the formula (I); tocol, a tocol derivative or a tocopherol, preferably TCP) from the non-polar phase, i.e. the non-polar solvent, and its purification if required, can be effected by procedures conventionally used in organic chemistry.

Advantages in the use of the catalyst in the process in accordance with the invention are the avoidance of corrosion, the avoidance of waste water contamination with chlorinated by-products, the recycling of non-reacted compound a) and the recycling of the catalyst. Further advantages are the high yields of (all-rac)-TCP, the high selectivity as well as the enabled ready isolation of the produced (all-rac)-TCP from the mixture after reaction, if the compound a) is TMHQ.

TCP e.g. can be converted into its acetate, succinate, and further known application forms by standard methods, e. g. as described in Ullmann's Encyclopedia of Industrial Chemistry, Vol. A27, $5^{th}$ edition, pages 484 to 485, VCH Verlagsgesellschaft mbH, D-69451 Weinheim, 1996. In contrast to e.g. TCP which is labile against oxidative conditions, the esters are more stable and more convenient to handle.

Process for the Manufacture of Formulations of α-tocopherol and its Esters

The α-tocopherol obtained by the process of the present invention or its esters obtained therefrom according to standard methods can further be formulated by any method known to the person skilled in the art, e.g. as those disclosed in U.S. Pat. No. 6,162,474, U.S. 2001/0009679, U.S. Pat. Nos. 6,180,130, 6,426,078, 6,030,645, 6,150,086, 6,001,554, 5,938,990, 6,530,684, 6,536,940, U.S. 2004/0053372, U.S. Pat. Nos. 5,668,183, 5,891,907, 5,350,773, 6,020,003, 6,329,423, WO 96/32949, U.S. Pat. No. 5,234,695, WO 00/27362, EP 0 664 116, U.S. 2002/0127303, U.S. Pat. Nos. 5,478,569, 5,925,381, 6,651,898, 6,358,301, 6,444,227, WO 96/01103 and WO 98/15195.

The following examples will illustrate preferred embodiments within the scope of the present invention. These examples are solely for the purpose of illustration and are not to be construed as limitations of the present invention as many variations thereof are possible without departing from the purview and spirit of the invention.

EXAMPLES

General Remarks

TMHQ (98%, Fluka in Buchs, Switzerland) was used without further purification. Isophytol (97%, Teranol in Lalden, Switzerland) was added with a Metrohm 665 Dosimat. $Gd(OSO_2CF_3)_3$ is commercially obtainable, e.g. in 98% purity from Aldrich (in Buchs, Switzerland). The 1:1-mixture of ethylene carbonate and propylene carbonate came from Huntsman (Huston, Tex.; Lot 8N400).

The crude products were analyzed by gas chromatography (GC). All reactions were carried out under argon.

Examples A–C

Preparation of (all-rac)-TCP Starting from IP

In a 200 ml four-necked flask equipped with a mechanical stirrer, a water separator and a reflux condenser, 7.53 g (50 mmol) of TMHQ, varying amounts of the catalyst $Gd(OSO_2CF_3)_3$ (amount based on IP; see table 1), 50 ml of a mixture of ethylene carbonate and propylene carbonate (v/v=1:1) and 50 ml of heptane were heated up under argon atmosphere to reflux (oil bath: 140 to 145° C.). 11.9 ml (33 mmol) of IP were added at a rate of 0.6 ml/minute. Approximately 0.2 ml of water were distilled off as mixture with heptane after complete addition of the IP. Afterwards the heptane was destined off to complete the reaction at a higher temperature. Therefore, the reaction mixture was heated for 22 hours at 125 to 130° C. Then it was cooled down to 80° C. 50 ml of heptane were added to the carbonate phase. The reaction mixture was stirred for an additional 10 minutes at 50° C. The heptane layer was separated and the heptane evaporated under reduced pressure. A viscous oil was obtained and analyzed by GC using the internal standard. The yield of (all-rac)-TCP (see table 1) is based on IP. The carbonate layer with the non-reacted TMHQ and the catalyst $Gd(OSO_2CF_3)_3$ was recycled.

TABLE 1

Influence of the amount of catalyst on the production of TCP

| Example | Gd(OSO$_2$CF$_3$)$_3$ [mol %] | yield of TCP [%] |
|---|---|---|
| A | 1 | 91.4 |
| B | 0.5 | 89.8 |
| C | 0.2 | 87.6* |

*reaction time = 20 hours; all other cases 22 hours.

Example D

Preparation of (all-rac)-TCP Starting from Phytyl Acetate

In a 200 ml four-necked flask equipped with a mechanical stirrer, a water separator and a reflux condenser, 7.54 g (49.5 mmol) of TMHQ, 202.2 mg (1 mol % based on phytyl acetate) of Gd(OSO$_2$CF$_3$)$_3$, 40 g of ethylene carbonate and 15 ml of heptane were heated up under argon atmosphere to reflux (oil bath: 145° C., stirring: 400 rotations per minute). 11.17 g (32.79 mmol) of phytyl acetate were dissolved in 35 ml of heptane and added through a dropping funnel within 1 hour and 15 minutes. The dropping funnel was washed with 3 ml of heptane. Approximately 0.2 ml of water were distilled off after complete addition of the phytyl acetate. The heptane was distilled off within approximately 10 minutes to complete the reaction at a higher temperature. Thus, the reaction mixture was heated for 1 hour and 45 minutes at 125 to 130° C. Afterwards it was cooled to 80° C. and 50 ml of heptane were added to the mixture. The reaction mixture was stirred for an additional 10 minutes at 50° C. The heptane layer was separated and the heptane evaporated under reduced pressure starting at 100 mbar (40° C.) and going to 10 mbar within 1 hour. 14.45 g of a viscous oil was isolated in 91.54% purity (GC, internal standard). Yield: 13.23 g of (all-rac)-TCP, 93.6% based on phytyl acetate.

Example E

Preparation of (all-rac)-TCP Starting from Phytyl Benzoate

In a 200 ml four-necked flask equipped with a mechanical stirrer, a water separator and a reflux condenser, 7.54 g (49.5 mmol) of TMHQ, 203.9 mg (1 mol % based on phytyl benzoate) of Gd(OSO$_2$CF$_3$)$_3$, 40 g of ethylene carbonate and 25 ml of heptane were heated up under argon atmosphere to reflux (oil bath: 145° C., stirring: 400 rotations per minute). 13.22 g (32.82 mmol) of phytyl benzoate were dissolved in 25 ml of heptane and added through a dropping funnel within 1 hour and 20 minutes. The dropping funnel was washed with 3 ml of heptane. Approximately 0.6 ml of water were distilled off after complete addition of the IP. The heptane was distilled off within approximately 10 minutes to complete the reaction at a higher temperature. Therefore, the reaction mixture was heated for 2 hours and 30 minutes at 125 to 130° C. Afterwards it was cooled to 80° C. and 50 ml heptane were added to the mixture. The reaction mixture was stirred for additional 10 minutes at 50° C. The heptane layer was separated and the heptane evaporated under reduced pressure starting at 100 mbar (40° C.) and going to 10 mbar within 1 hour. 17.0 g of a high viscous oil with a small amount of solid was isolated in 79.04% purity (GC, internal standard). Yield: 13.44 g of (all-rac)-TCP, 95.0% based on phytyl benzoate.

Comparison Example F

Preparation of (all-rac)-TCP in Heptane

In a 200 ml four-necked flask equipped with a mechanical stirrer, a water separator and a reflux condenser, 7.54 g (49.5 mmol) of TMHQ, 200.7 mg (1 mol % based on IP) of Gd(OSO$_2$CF$_3$)$_3$ and 50 ml of heptane were heated up under argon atmosphere to reflux (oil bath: 145° C., stirring: 400 rotations per minute). 11.9 ml (33 mmol) of IP were added at a rate of 0.6 ml/minute. Traces of water were distilled off after complete addition of the IP. Afterwards the reaction mixture was heated for 27 hours at 98 to 101° C. Then it was cooled to room temperature and filtered off through cellite/speedex. The heptane was evaporated under reduced pressure starting at 100 mbar (40° C.) and going to 10 mbar within 1 hour. 14.26 g of a orange precipitate was isolated in 28.68% purity (GC, internal standard). Yield 4.09 g of (all-rac)-TCP, 28.8% based on IP.

TABLE 2

Summarisation of examples D–F

| example | compound b) | solvent | yield [% based on compound b)] |
|---|---|---|---|
| D | phytyl acetate | ethylene carbonate + heptane | 93.6 |
| E | phytyl benzoate | ethylene carbonate + heptane | 95.0 |
| F | isophytol | heptane | 28.8 |

The invention claimed is:

1. A process for the manufacture of compounds represented by the following formula (I) with X$^1$, X$^2$ and X$^3$ being independently from each other hydrogen or methyl

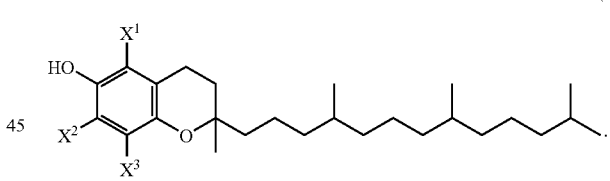

by the catalyzed reaction of a compound a) represented by the following formula (II)

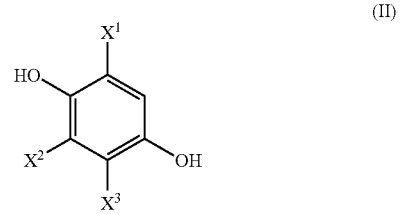

with a compound b) selected from the group consisting of phytol, isophytol and (iso)phytol derivatives represented by the following formulae (III) and (IV) with R=C$_{2-5}$-alkanoyloxy, benzoyloxy, mesyloxy, benzenesulfonyloxy or tosyloxy,

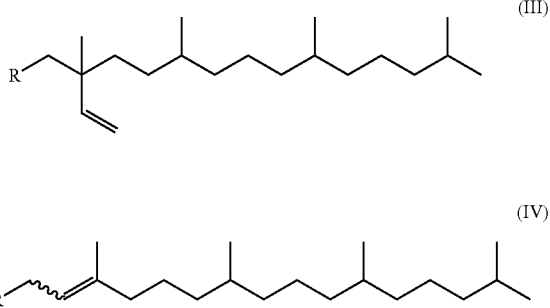

characterized in that the reaction is carried out in the presence of gadolinium trifluoromethanesulfonate, Gd(OSO$_2$CF$_3$)$_3$, as the catalyst in a biphasic solvent system.

2. The process according to claim 1 wherein the biphasic solvent system essentially consists of a polar organic solvent and a non-polar organic solvent,
wherein the compound a) is dissolved or suspended in the polar organic solvent, and the molar amount of compound a) is at least about 25% higher than the molar amount of compound b);
wherein the polar phase containing the polar organic solvent, the catalyst and non-reacted compound a) is separated from the non-polar phase containing the non-polar organic solvent and the produced compound of formula (I); and
wherein the polar phase is recycled back in the catalyzed reaction according to claim 1.

3. The process as claimed in claim 1, wherein the C$_{2-5}$-alkanoyloxy is selected from the group consisting of acetyloxy, propionyloxy and pivaloyloxy.

4. The process as claimed in claim 1, wherein compound a) is reacted with a compound b) selected from the group consisting of phytol, isophytol and (iso)phytol derivatives represented by the formulae (III) and (IV) with R=acetyloxy or benzoyloxy.

5. The process as claimed in claim 4, wherein the compound a) is 2,3,5-trimethylhydroquinone.

6. The process as claimed in claim 5, wherein 2,3,5-trimethylhydroquinone is reacted with phytol or isophytol, preferably with isophytol, to α-tocopherol.

7. The process as claimed in claim 1, wherein the biphasic solvent system consists essentially of a polar solvent and a non-polar solvent, the polar solvent being at least a cyclic carbonate, and the non-polar solvent being at least a linear, branched or cyclic C$_{5-15}$-alkane.

8. The process as claimed in claim 7, wherein the cyclic carbonate is ethylene carbonate and/or propylene carbonate.

9. The process as claimed in claim 7, wherein the linear, branched or cyclic C$_{5-15}$-alkane is hexane, heptane, octane, cyclohexane, methylcyclohexane or a mixture thereof, preferably heptane.

10. The process as claimed in claim 7, wherein the cyclic carbonate is ethylene carbonate or propylene carbonate and the linear, branched or cyclic C$_{5-15}$-alkane is hexane, heptane, octane, cyclohexane, methylcyclohexane or a mixture thereof, preferably heptane.

11. The process as claimed in claim 6, wherein the biphasic solvent system consists essentially of a polar solvent and a non-polar solvent, the polar solvent being at least a cyclic carbonate, and the non-polar solvent being at least a linear, branched or cyclic C$_{5-15}$-alkane; preferably the cyclic carbonate being ethylene carbonate or propylene carbonate, and the linear, branched or cyclic C$_{5-15}$-alkane being hexane, heptane, octane, cyclohexane, methylcyclohexane or a mixture thereof, especially heptane.

12. The process as claimed in claim 7, wherein the volume ratio of the polar solvent to the non-polar solvent in said biphasic solvent system is in the range from about 5:1 to about 1:10, preferably from about 3:1 to about 1:5, especially from about 2:1 to about 1:1.25.

13. The process as claimed in claim 11, wherein the volume ratio of the polar solvent to the non-polar solvent in said biphasic solvent system is in the range from about 5:1 to about 1:10, preferably from about 3:1 to about 1:5, especially from about 2:1 to about 1:1.25.

14. The process as claimed in claim 7, wherein from about 0.5 ml to about 2.0 ml, preferably from about 0.6 ml to about 1.75 ml, more preferably from about 0.8 ml to about 1.6 ml of a polar organic solvent are used per mmol of compound b).

15. The process as claimed in claim 13, wherein from about 0.5 ml to about 2.0 ml, preferably from about 0.6 ml to about 1.75 ml, more preferably from about 0.8 ml to about 1.6 ml of a polar organic solvent are used per mmol of compound b).

16. The process as claimed in claim 1, wherein the relative amount of the catalyst Gd(OSO$_2$CF$_3$)$_3$ to the amount of compound b) is from about 0.1 mol % to about 1.8 mol %, preferably from about 0.5 mol % to about 1.5 mol %, more preferably from about 0.8 to about 1.2 mol %.

17. The process as claimed in claim 11, wherein the relative amount of the catalyst Gd(OSO$_2$CF$_3$)$_3$ to the amount of compound b) is from about 0.1 mol % to about 1.8 mol %, preferably from about 0.5 mol % to about 1.5 mol %, more preferably from about 0.8 to about 1.2 mol %.

18. The process as claimed in claim 1, wherein the molar ratio of compound a) to compound b) present in the reaction mixture is from about 1.25:1 to about 3:1, preferably from about 1.35:1 to about 2.2:1, more preferably from about 1.5:1 to about 2:1.

19. The process as claimed in claim 11, wherein the molar ratio of compound a) to compound b) present in the reaction mixture is from about 1.25:1 to about 3:1, preferably from about 1.35:1 to about 2.2:1, more preferably from about 1.5:1 to about 2:1.

20. The process according to claim 1, wherein compound b) as such is added portionwise or continuously to a mixture of Gd(OSO$_2$CF$_3$)$_3$, the compound a) and the biphasic solvent system.

21. The process as claimed in claim 11, wherein compound b) as such is added portionwise or continuously to a mixture of Gd(OSO$_2$CF$_3$)$_3$, the compound a) and the biphasic solvent system.

22. The process as claimed in claim 1, wherein the reaction is carried out at temperatures from about 80° C. to about 160° C., preferably from about 90° C. to about 150° C., especially from about 100° C. to about 145° C.

23. The process as claimed in claim 11, wherein the reaction is carried out at temperatures from about 80° C. to about 160° C., preferably from about 90° C. to about 150° C., especially from about 100° C. to about 145° C.

24. A process for the manufacture of α-tocopherol esters and/or formulations of α-tocopherol and/or its esters wherein α-tocopherol obtained by a process according to claim 1 is used.

25. A process for the manufacture of α-tocopherol esters and/or formulations of α-tocopherol and/or its esters wherein α-tocopherol obtained by a process according to claim 6 is used.

26. A process for the manufacture of α-tocopherol esters and/or formulations of α-tocopherol and/or its esters wherein α-tocopherol obtained by a process according to claim 11 is used.

* * * * *